United States Patent
Kleiber et al.

(10) Patent No.: US 11,697,631 B2
(45) Date of Patent: Jul. 11, 2023

(54) PROCESS AND FACILITY FOR RECOVERING METHOXYPROPANOLS FROM AN AQUEOUS STREAM

(71) Applicants: Evonik Operations GmbH, Essen (DE); thyssenkrupp Industrial Solutions AG, Essen (DE)

(72) Inventors: Michael Kleiber, Hattersheim (DE); Willi Hofen, Rodenbach (DE)

(73) Assignees: Evonik Operations GmbH, Essen (DE); thyssenkrupp Industrial Solutions AG, Essen (DE)

( * ) Notice: Subject to any disclaimer, the term of this patent is extended or adjusted under 35 U.S.C. 154(b) by 0 days.

(21) Appl. No.: 17/995,468

(22) PCT Filed: Mar. 23, 2021

(86) PCT No.: PCT/EP2021/057423
§ 371 (c)(1),
(2) Date: Oct. 4, 2022

(87) PCT Pub. No.: WO2021/204531
PCT Pub. Date: Oct. 14, 2021

(65) Prior Publication Data
US 2023/0122837 A1    Apr. 20, 2023

(30) Foreign Application Priority Data
Apr. 6, 2020   (EP) .................................. 20168126

(51) Int. Cl.
*C07C 41/42*    (2006.01)

(52) U.S. Cl.
CPC ..................................... *C07C 41/42* (2013.01)

(58) Field of Classification Search
CPC ................................. C07C 41/42; C07C 41/38
See application file for complete search history.

(56) References Cited

U.S. PATENT DOCUMENTS

2004/0000473 A1*   1/2004   Hofen et al. ........... C07C 41/36
                                                                203/81

FOREIGN PATENT DOCUMENTS

| CN | 107032966 | 8/2017 |
|---|---|---|
| CN | 110330413 | 10/2019 |
| WO | 2004/000773 | 12/2003 |

OTHER PUBLICATIONS

International Search Report dated Jul. 5, 2021, in PCT/EP2021/057423, 5 pages.
Written Opinion dated Jul. 5, 2021, in PCT/EP2021/057423, 11 pages.

* cited by examiner

*Primary Examiner* — Rosalynd A Keys
(74) *Attorney, Agent, or Firm* — Grüneberg and Myers, PLLC

(57) ABSTRACT

A process can be used for recovering 1-methoxy-2-propanol and 2-methoxy-1-propanol from an aqueous effluent stream by liquid-liquid-extraction, followed by extractive distillation, distillation of methoxypropanols from the extraction solvent, and distillative separation of the methoxypropanol isomers. Recovered extraction solvent is recycled to the extraction and extractive distillation. Heat transfer from recovered extraction solvent to the extract fed to the extractive distillation reduces energy demand of the process. A facility for this process contains a countercurrent extraction column, an extractive distillation column, a solvent recovery distillation column, an isomer separation distillation column, and a heat exchanger for transferring heat from recovered extraction solvent to the extract fed to the extractive distillation.

14 Claims, 1 Drawing Sheet

Figure
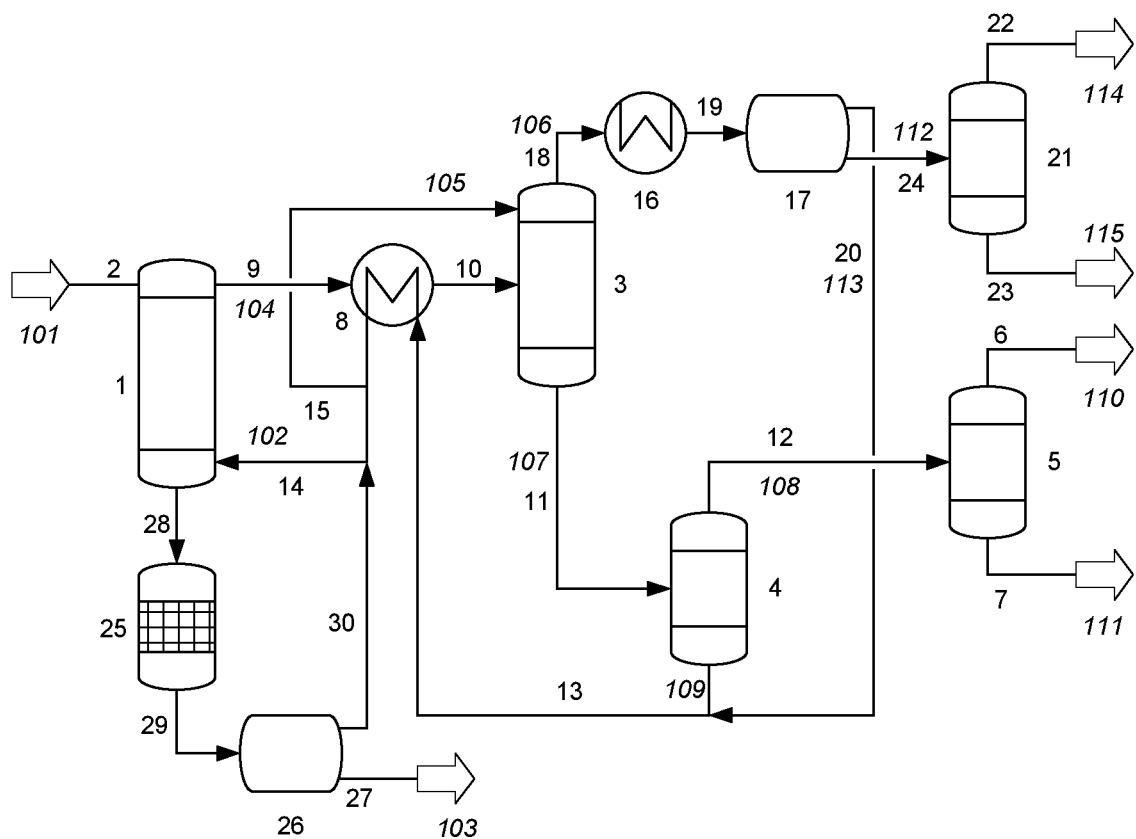

PROCESS AND FACILITY FOR RECOVERING METHOXYPROPANOLS FROM AN AQUEOUS STREAM

CROSS-REFERENCE TO RELATED APPLICATIONS

This application is the National Stage entry under §371 of International Application No. PCT/EP2021/057423, filed on Mar. 23, 2021, and which claims the benefit of priority to European Application No. 20168126.9, filed on Apr. 6, 2020. The content of each of these applications is hereby incorporated by reference in its entirety.

BACKGROUND OF THE INVENTION

Field of the Invention

The invention is directed at a process and a facility for recovering 1-methoxy-2-propanol and 2-methoxy-1-propanol from an aqueous effluent stream formed in a process for making propene oxide by epoxidation of propene with hydrogen peroxide in a methanol solvent.

Description of Related Art

The epoxidation of propene with hydrogen peroxide in a methanol solvent in the presence of a titanium zeolite epoxidation catalyst has become a major industrial process for manufacturing propene oxide. Since the reaction forms water from hydrogen peroxide and hydrogen peroxide is used as an aqueous solution, this process produces an aqueous effluent stream. This aqueous effluent stream usually contains dissolved 1-methoxy-2-propanol and 2-methoxy-1-propanol formed as byproducts from reaction of propene oxide with solvent methanol. Recovering the methoxypropanols from the aqueous effluent stream is desirable not only because they have commercial value but also for reducing the TOC of the aqueous effluent stream and thereby reducing the size of the facility necessary for treating the aqueous effluent stream for discharge into a water body.

WO 99/23052 describes the recovery of byproducts 1-chloro-3-methoxy-2-propanol, 1-chloro-2-methoxy-3-propanol, 1,3-dichloropropanol, 2,3-dichloropropanol and 1-chloro-2,3-dihydroxypropane by liquid-liquid-extraction of an aqueous effluent, resulting from preparing epichlorohydrin by epoxidation of allylchloride with hydrogen, with a trialklyphosphine as extractant. The document suggests using the same extraction method for recovering by-products from an aqueous effluent resulting from epoxidation of propene with hydrogen peroxide.

WO 2006/006981 describes recovery of propylene glycol and propylene glycol monomethylether from an aqueous stream by countercurrent liquid-liquid-extraction with liquid propene or propane. However, this requires operating the extraction at a pressure of more than 13 bar and a large volume of extractant due to unfavorable distribution coefficients.

WO 2004/000773 describes a process for recovering 1-methoxy-2-propanol and 2-methoxy-1-propanol from an aqueous effluent stream of propene oxide production where the stream is subjected to distillation to provide an overhead product enriched in the methoxypropanols, this overhead product is dewatered by azeotropic distillation, extractive distillation or pervaporation and the resulting anhydrous mixture of 1-methoxy-2-propanol and 2-methoxy-1-propanol is distilled to separate the methoxypropanol isomers.

CN 110272333 A and CN 110330413 A disclose methods for recovering methoxypropanols from an aqueous effluent where the stream is subjected to distillation to provide an overhead product enriched in the methoxypropanols and this overhead product is extracted with a solvent by liquid-liquid extraction in a mixer settler unit or a countercurrent extraction column. Disclosed extraction solvents are diisobutyl ketone (2,6-dimethylheptan-4-one), isobutyl acetone (5-methylhexan-2-one), 4,6-dimethylheptan-2-one, 1,3-dimethylbutanol and diisobutyl methanol (2,6-dimethylheptan-4-ol). The extract is distilled to recover the extraction solvent as a bottoms product and a mixture comprising water and methoxypropanols as an overhead product, followed by dewatering this mixture in a distillation providing an anhydrous bottoms product comprising methoxypropanols and an overhead product comprising water and methoxypropanols which is recycled the aqueous feed to the extraction step. CN 110330413 A also discloses recovering methoxypropanols from the aqueous effluent without prior concentration by distillation, carrying out the extraction at increased temperatures of 95-125° C.

CN 110606799 A discloses a method for recovering byproducts from a process for making propene oxide from propene and hydrogen peroxide which comprises a distillation to provide an aqueous overhead product enriched in methoxypropanols and extracting this overhead product with trifluorodichloroethane or trifluorotrichloroethane. However, the use of these compounds as solvents is banned or will be banned under the Montreal protocol.

T. Zhao et al., Chem. Eng. Res. Des. 132 (2018) 399-408 and CN 107032966 disclose recovery of 1-methoxy-2-propanol from an aqueous solution by liquid-liquid extraction with 2-ethylhexanoic acid as extraction solvent, subjecting the extract to extractive distillation using the same extraction solvent to provide an anhydrous bottoms product comprising 1-methoxy-2-propanol and 2-ethylhexanoic acid, separating this bottoms product by distillation and recycling the extraction solvent. The recovery method is found to be more energy efficient than only extractive distillation with 2-ethylhexanoic acid, heteroazeotrope dewatering with chloroform or a combination of liquid-liquid extraction with the heteroazeotrope dewatering.

SUMMARY OF THE INVENTION

The inventor of the present invention has now found a process for recovering 1-methoxy-2-propanol and 2-methoxy-1-propanol from an aqueous effluent stream resulting from producing propene oxide by epoxidation of propene with hydrogen peroxide in a methanol solvent, which uses a combination of extraction and extractive distillation with a specific heat recovery which significantly reduces energy consumption of the recovery process. The process can be used for aqueous effluent streams containing residual solvent methanol and by-product organic amines and efficiently reduces the content of organic impurities in the aqueous effluent stream without a need for heating this stream for distillation.

Subject of the invention is a process for recovering 1-methoxy-2-propanol and 2-methoxy-1-propanol from an aqueous effluent stream, comprising the steps of
a) extracting the aqueous effluent stream with an extraction solvent stream in a countercurrent extraction column at a temperature of from 20 to 60° C. to provide a raffinate stream and an extract stream, b) heating the extract stream by passing it through a heat exchanger on the heat uptake side of the heat exchanger to provide a heated extract stream, c) subjecting the heated extract stream to an extractive distillation in an extractive distillation column having an inlet for extraction solvent above an inlet for the heated extract stream, providing a first overhead stream enriched in water and a first bottoms stream depleted in water relative to said heated extract stream, d) distilling the first bottoms stream in a solvent recovery distillation column to provide a second overhead stream comprising 1-methoxy-2-propanol and 2-methoxy-1-propanol and a second bottoms stream comprising recovered extraction solvent, e) distilling the second overhead stream in an isomer separation distillation column to provide a third overhead stream comprising 1-methoxy-2-propanol and a third bottoms stream comprising 2-methoxy-1-propanol, f) cooling the second bottoms stream by passing it through the heat exchanger on the heat delivery side of the heat exchanger to provide a recovered extraction solvent stream, and g) passing a part of the recovered extraction solvent stream as extraction solvent stream to step a) and a part of the recovered extraction solvent stream as extraction solvent to step c).

A further subject of the invention is a facility for recovering 1-methoxy-2-propanol and 2-methoxy-1-propanol from an aqueous effluent stream, comprising a countercurrent extraction column having a feed inlet, an extraction solvent inlet, a raffinate outlet and an extract outlet;

an extractive distillation column having a feed inlet, an extraction solvent inlet above the feed inlet, an overhead product outlet and a bottoms product outlet;

a solvent recovery distillation column having a feed inlet, an overhead product outlet and a bottoms product outlet;

an isomer separation distillation column having a feed inlet, an overhead product outlet and a bottoms product outlet;

a heat exchanger having a heat supply side and a heat uptake side, each having an inlet and an outlet;

a conduit connecting the extract outlet of the countercurrent extraction column with the inlet of the heat uptake side of the heat exchanger;

a conduit connecting the outlet of the heat uptake side of the heat exchanger with the feed inlet of the extractive distillation column;

a conduit connecting the bottoms product outlet of the extractive distillation column with the feed inlet of the solvent recovery distillation column;

a conduit connecting the overhead product outlet of the solvent recovery distillation column with the feed inlet of the isomer separation distillation column;

a conduit connecting the bottoms product outlet of the solvent recovery distillation column with the inlet of the heat supply side of the heat exchanger;

and conduits connecting the outlet of the heat supply side of the heat exchanger with the extraction solvent inlet of the countercurrent extraction column and the extraction solvent inlet of the extractive distillation column.

BRIEF DESCRIPTION OF DRAWINGS

The FIG. 1 shows an embodiment of the facility of the invention comprising an additional light impurity distillation column and a coalescer for recovering extraction solvent from the raffinate stream leaving the extraction column. Reboilers and condensers of distillation columns have been omitted for clarity. Reference numbers in italics refer to process features.

DETAILED DESCRIPTION OF THE INVENTION

The process of the invention recovers 1-methoxy-2-propanol and 2-methoxy-1-propanol from an aqueous effluent stream by extracting this stream with an extraction solvent stream in a countercurrent extraction column.

The aqueous effluent stream from which the methoxypropanols are recovered is preferably an effluent stream from producing propene oxide by epoxidation of propene with hydrogen peroxide in a methanol solvent. The aqueous effluent stream can be a bottoms product from a distillation unit for recovering methanol solvent but is preferably a condensate resulting from distilling water from such a bottoms product. If a multi-stage distillation or evaporation unit is used for distilling water from the bottoms product, the aqueous effluent stream is preferably a condensate from the first distillation or evaporation stage.

The aqueous effluent stream, which is extracted in the process of the invention, preferably comprises 1-methoxy-2-propanol and 2-methoxy-1-propanol in a combined amount of from 1 to 10% by weight, more preferably from 2 to 6% by weight. The process of the invention can be carried out with an aqueous effluent stream having a low content of methoxypropanols and does not require a distillation step prior to extraction for concentrating methoxypropanols by distilling off a close to azeotropic mixture of water and methoxypropanols like some of the prior art processes.

The aqueous effluent stream may contain further components in addition to water and the methoxypropanols. The aqueous effluent stream preferably comprises from 0.1 to 5% by weight of methanol, more preferably from 1 to 3% by weight. The process of the invention can recover methoxypropanols from an aqueous effluent stream having such content of methanol without a need for purging a stream containing both methanol and methoxypropanols from the process, as is the case for some of the prior art processes. The aqueous effluent stream may also contain small amounts of ammonia and volatile organic amines such as ethylamine. If ammonia or organic amines are present in the aqueous effluent stream, the extraction is preferably carried out with a non-acidic extraction solvent.

The extraction solvent used for extracting the aqueous effluent stream preferably comprises at least one hydrogen acceptor functional group. Extraction solvents with a hydrogen acceptor functional group can form a hydrogen bond between the hydrogen acceptor functional group and the hydroxyl group of the methoxypropanols which provides a more favorable partition coefficient of the methoxypropanols between the aqueous phase and the extractant phase than achieved with non-polar extraction solvents having no hydrogen acceptor functional group. The hydrogen acceptor functional group is preferably an aliphatic hydroxyl group, a ketone carbonyl group, a sulfoxide group, a sulfone group, a carboxamide group, a phosphine oxide group or a phosphoric ester group and the extraction solvent may contain several of these groups as well as combinations of these groups. In a preferred embodiment, the extraction solvent is an aliphatic alcohol having from 7 to 14 carbon atoms, most preferably 2-ethylhexanol. The preferred extraction solvents do not contain functional groups that will react with the methoxypropanols at elevated temperatures reached in subsequent distillation stages of the process, unlike the prior art extraction solvent 2-ethylhexanoic acid, which can react with 2-ethylhexanol in an esterification reaction to provide by-products that would accumulate in the process and change the extracting properties of the extraction solvent.

The extraction solvent used for extracting the aqueous effluent stream preferably has a solubility in water at 20° C. of less than 1 g/kg and a boiling point at 1 bar of at least 160° C. to minimize loss of extractant solvent with the aqueous raffinate stream and allow for efficient distillative separation of the methoxypropanols from the extraction solvent. Extraction solvents forming an azeotrope with water can be used if they form a low boiling heteroazeotrope.

The extraction of the aqueous effluent stream is carried out at a temperature of from 20 to 60° C., preferably from 30 to 45° C., to maintain a broad miscibility gap between water and the extraction solvent, providing both a low solubility of the extraction solvent in the aqueous raffinate stream and a low water solubility in the extract stream. Carrying out the extraction in this temperature range also allows extracting an aqueous effluent stream which contains low boiling impurities, such as methanol, which would evaporate at higher extraction temperatures.

The extraction is carried out in a countercurrent extraction column, preferably in an extraction column providing a separation efficiency of from 5 to 20 theoretical extraction stages. The size and the separation efficiency of the countercurrent extraction column and the flow rate of the extraction solvent stream are preferably chosen to extract more than 95% of the methoxypropanols from the aqueous effluent stream, preferably more than 98% and most preferably more than 99% of the methoxypropanols.

The raffinate stream from the countercurrent extraction column is preferably passed through a coalescer for coalescing droplets of extraction solvent dispersed in the aqueous raffinate stream. The organic phase formed by coalescing these droplets is recycled to the extraction step for supplying extraction solvent, preferably to the extraction solvent stream entering the extraction column.

The extract stream obtained in the extraction step is heated by passing it through a heat exchanger on the heat uptake side of the heat exchanger to provide a heated extract stream which is then subjected to an extractive distillation.

The heated extract stream is subjected to an extractive distillation in an extractive distillation column which has an inlet for the extraction solvent above the inlet for the heated extract stream, preferably at the top of the extractive distillation column. The extractive distillation provides a first overhead stream enriched in water and a first bottoms stream depleted in water relative to the heated extract stream which is fed to the extractive distillation column. The extractive distillation is preferably operated at a pressure of from 0.1 to 2 bar, more preferably 0.2 to 0.3 bar, at the column top. The flow rate of extraction solvent fed to the extractive distillation, the reflux ratio and the number of theoretical separation stages of the stripping section below the inlet for the heated extract stream, of the extraction section between the inlet for the heated extract stream and the inlet for the extraction solvent and of the rectification section above the inlet for the extraction solvent are preferably chosen to provide a first overhead stream comprising less than 2% of the methoxypropanols contained in the heated extract stream which is fed to the extractive distillation column and a first bottoms stream comprising less than 0.1% of the water contained in the heated extract stream, both values being calculated on a weight basis. This way, water is separated with the first overhead stream from the methoxypropanols which are obtained as a mixture with the extraction solvent in the first bottoms stream. When the extraction solvent is an aliphatic alcohol having from 7 to 14 carbon atoms, such as 2-ethylhexanol or 1-nonanol, the flow rate of extraction solvent fed to the extractive distillation column is preferably from 10 to 25 times the amount of methoxypropanols fed to the extractive distillation column with the heated extract stream, calculated on a weight basis.

The first bottoms stream from the extractive distillation column is then further distilled in a solvent recovery distillation column to provide a second overhead stream comprising the methoxypropanols, i.e. 1-methoxy-2-propanol and 2-methoxy-1-propanol, and a second bottoms stream comprising recovered extraction solvent. The solvent recovery distillation is preferably operated at a pressure of from 0.1 to 1.0 bar, more preferably 0.1 to 0.3 bar, at the column top. The reflux ratio and the number of theoretical separation stages in the stripping section and the rectification section of the solvent recovery distillation column are preferably chosen to provide a second overhead stream comprising less than 0.1% of the extraction solvent contained in the first bottoms stream which is fed to the solvent recovery distillation column and a second bottoms stream comprising less than 2% of the methoxypropanols contained in the first bottoms stream, both values being calculated on a weight basis.

The second overhead stream from the solvent recovery distillation is distilled in an isomer separation distillation column to provide a third overhead stream comprising 1-methoxy-2-propanol and a third bottoms stream comprising 2-methoxy-1-propanol. The isomer separation distillation column is preferably operated at a pressure of from 0.1 to 2 bar, more preferably 0.2 to 0.6 bar, at the column top. The reflux ratio and the number of theoretical separation stages in the stripping section and the rectification section of this distillation column are preferably chosen to provide a third overhead stream comprising less than 0.5% of the 2-methoxy-1-propanol contained in the second overhead stream which is fed to the isomer separation distillation column and a third bottoms stream comprising less than 0.5% of the 1-methoxy-2-propanol contained in the second overhead stream, both values being calculated on a weight basis.

The second bottoms stream from the solvent recovery distillation is passed through the heat delivery side of the heat exchanger used for heating the extract stream, which cools the second bottoms stream and provides a recovered extraction solvent stream. An additional cooler may be used downstream of the heat exchanger to further cool the second bottoms stream and provide the recovered extraction solvent stream at the temperature used in the extraction step. Heat exchange between the second bottoms stream, which delivers heat, and the extract stream, which takes up the heat from the second bottoms stream, leads to a significant reduction in the heat demand of the extractive distillation compared to prior art processes using extractive distillation without such heat recovery.

A part of the recovered extraction solvent stream is passed to the extraction step as extraction solvent stream and another part of the recovered extraction solvent stream is passed to the extractive distillation step as extraction solvent. Preferably, only a small fraction of the recovered extraction solvent stream, preferably less than 0.02% by weight, is purged from the process to prevent accumulation of high boiling by-products in the extraction solvent, with the remainder being recycled either to the extraction step or the extractive distillation step.

When an extraction solvent is used which forms a heteroazeotrope with water, the first overhead stream from the extractive distillation column preferably is condensed and separated into an aqueous phase stream and an organic phase stream. The separated organic phase stream is then either combined with the second bottoms stream from the solvent recovery distillation or is passed to the extractive distillation for supplying extraction solvent, preferably passing it to the inlet for extraction solvent on the extractive distillation column.

When the aqueous effluent stream contains compounds which are more volatile than water, such as methanol, the aqueous phase stream separated from the condensed first overhead stream is preferably distilled in a light impurity distillation column to provide a fourth overhead stream which is enriched in these volatile compounds, compared to the separated aqueous phase. If the extraction solvent does not form a heteroazeotrope with water, the entire first overhead stream from the extractive distillation can be fed to the light impurity distillation column. The light impurity distillation is particularly advantageous if the aqueous effluent stream contains residual methanol solvent from a propene epoxidation process and can lead to a significant reduction in the chemical oxygen demand (COD) of the aqueous streams leaving the process which leads to savings in a subsequent waste water treatment.

When the extractive distillation column is operated at a higher bottoms temperature than the isomer separation distillation column, the process of the invention may be advantageously carried out with heat supply from the second bottoms stream exiting the solvent recovery distillation to the column reboiler of the isomer separation distillation column. In a similar way, heat can also be supplied from the second bottoms stream to the column reboiler of the light impurity distillation column.

The process of the invention is preferably carried out in a facility of the invention as described further above and most preferably in a facility as shown in the figure.

The facility of the invention comprises a countercurrent extraction column (1) which has a feed inlet (2), an extraction solvent inlet, a raffinate outlet and an extract outlet. For use with an extraction solvent having a density lower than the density of water, the feed inlet (2) is at the upper end of the extraction column (1), the extraction solvent inlet is at the lower end of the extraction column (1), the raffinate outlet is at the bottom of the extraction column (1) and the extract outlet is at the upper end of the extraction column (1), preferably located higher than the feed inlet (2). The extraction column can be a packed column or a sieve tray column which can be operated with or without pulsation. The extraction column may also be a rotating disc contactor or an asymmetric rotating disc contactor or an agitated Kühni extraction column.

The facility of the invention further comprises an extractive distillation column (3) which has a feed inlet, an extraction solvent inlet above the feed inlet, an overhead product outlet and a bottoms product outlet. Any known type of extractive distillation column may be used, such as a tray column or a column with a random packing or a structured packing, with structures packings being preferred. The extractive distillation column may also have a combination of trays and packings in different sections of the column.

The facility of the invention also comprises a solvent recovery distillation column (4) which has a feed inlet, an overhead product outlet and a bottoms product outlet. A conduit (11) connects the bottoms product outlet of the extractive distillation column (3) with the feed inlet of the solvent recovery distillation column (4). Any known type of distillation column may be used for the solvent recovery distillation, such as a tray column or a column with a random packing or a structured packing, with structures packings being preferred.

The facility of the invention comprises a heat exchanger (8) for recovering heat from the bottoms product of the solvent recovery distillation column (4) and using this heat for heating the extract from the countercurrent extraction column (1) before feeding it to the extractive distillation column (3). The heat exchanger (8) has a heat supply side and a heat uptake side, each of these sides having an inlet and an outlet. The heat exchanger can be a cross-flow heat exchanger or preferably a countercurrent heat exchanger. Any type of liquid-liquid heat exchanger with flow separation between the heat uptake side and the heat delivery side may be used, such as a tube bundle heat exchanger or preferably a plate heat exchanger. A conduit (9) connects the extract outlet of the countercurrent extraction column (1) with the inlet of the heat uptake side of the heat exchanger (8) and a conduit (10) connects the outlet of the heat uptake side of the heat exchanger (8) with the feed inlet of the extractive distillation column (3). A conduit (13) connects the bottoms product outlet of the solvent recovery distillation column (4) with the inlet of the heat supply side of the heat exchanger (8) and conduits (14, 15) connect the outlet of the heat supply side of the heat exchanger (8) with the extraction solvent inlet of the countercurrent extraction column (1) and with the extraction solvent inlet of the extractive distillation column (3).

The facility of the invention further comprises an isomer separation distillation column (5) which has a feed inlet, an overhead product outlet (6) and a bottoms product outlet (7). A conduit (12) connects the overhead product outlet of the solvent recovery distillation column (4) with the feed inlet of the isomer separation distillation column (5). Any type of distillation column may be used for the isomer separation distillation, such as a tray column or a column with a random packing or a structured packing, with structures packings being preferred.

For use with an extraction solvent, which forms a heteroazeotrope with water, the facility of the invention preferably also comprises an overhead condenser (16) which has an inlet and an outlet; a phase separation vessel (17) which has an inlet, an outlet for organic phase and an outlet for aqueous phase; a conduit (18) which connects the overhead product outlet of the extractive distillation column (3) with the inlet of the overhead condenser (16); a conduit (19) which connects the outlet of the overhead condenser (16) with the inlet of the phase separation vessel (17); and a conduit (20) which connects the outlet for organic phase of the phase separation vessel (17) either with the conduit (13) connecting the bottoms product outlet of the solvent recovery distillation column (4) with the inlet of the heat supply side of the heat exchanger (8) or with the conduit (15) connecting the outlet of the heat supply side of the heat exchanger (8) with the extraction solvent inlet of the extractive distillation column (3), with the first alternative for conduit (20) being preferred.

In a preferred embodiment, the facility of the invention additionally comprises a light impurity distillation column (21) which has a feed inlet, an overhead product outlet (22) and a bottoms product outlet (23). The feed inlet of the light impurity distillation column (21) can be connected to the overhead product outlet of the extractive distillation column (3). When the facility comprises a phase separation vessel (17) as described in the preceding paragraph, the feed inlet of the light impurity distillation column (21) is preferably connected through a conduit (24) with the outlet for aqueous phase of the phase separation vessel (17). Any type of distillation column may be used for the light impurity distillation column, such as a tray column or a column with a random packing or a structured packing, with structured packings being preferred.

In another preferred embodiment, the facility of the invention additionally comprises a coalescer (25) which has an inlet and an outlet; a phase separator (26) which has an inlet, an outlet for organic phase and an outlet (27) for aqueous phase; a conduit (28) which connects the raffinate outlet of the countercurrent extraction column (1) with the inlet of the coalescer (25); a conduit (29) which connects the outlet of the coalescer (25) with the inlet of the phase separator (26); and a conduit (30) which connects the outlet for organic phase of the phase separator (26) with the extraction solvent inlet of the countercurrent extraction column (1). The coalescer preferably contains nets, meshes or packings of hydrophobic fibers or a packing with a hydrophobic surface.

EXAMPLES

Example 1

The recovery of 1-methoxy-2-propanol and 2-methoxy-1-propanol from an aqueous effluent stream, comprising 93.26 wt.-% water, 2.66 wt.-% 1-methoxy-2-propanol (1MPOL), 2.08 wt.-% 2-methoxy-1-propanol (2MPOL), 0.32 wt.-% 1,2-propanediol (DIOL), 1.31 wt.-% methanol and 0.37 wt.-% other components, using 2-ethylhexanol (2EH) as extraction solvent was calculated for a process as shown in the figure (with an additional purge stream (116) of recovered extraction solvent to the inlet of the light impurity distillation column) using the Aspen Plus simulation software package. Calculation was for extraction at 40° C. with a weight ratio of extraction solvent stream to aqueous effluent stream of about 3 and extractive distillation at 0.25 bar with a weight ratio of extraction solvent to extract stream of about 0.25. Table 1 shows the calculated flow rates and composition of streams in the process.

TABLE 1

| Stream No. | Total flow kg/h | $H_2O$ wt.-% | 1MPOL wt.-% | 2MPOL wt.-% | DIOL wt.-% | MeOH wt.-% | 2EH wt.-% |
|---|---|---|---|---|---|---|---|
| 101 | 23680 | 93.26 | 2.66 | 2.08 | 0.32 | 1.31 | 0.00 |
| 102 | 70000 | 0.01 | 0.00 | 0.00 | 0.00 | 0.01 | 99.97 |
| 103 | 20207 | 98.83 | 0.00 | 0.01 | 0.37 | 0.37 | 0.12 |
| 104 | 73473 | 2.89 | 0.86 | 0.67 | 0.01 | 0.33 | 95.21 |
| 105 | 18020 | 0.01 | 0.00 | 0.00 | 0.00 | 0.01 | 99.97 |
| 106 | 2675 | 79.32 | 0.13 | 0.00 | 0.00 | 9.09 | 10.28 |
| 107 | 88817 | 0.00 | 0.71 | 0.56 | 0.01 | 0.00 | 98.73 |
| 108 | 1117 | 0.00 | 56.10 | 43.90 | 0.00 | 0.00 | 0.00 |
| 109 | 87700 | 0.00 | 0.00 | 0.00 | 0.01 | 0.00 | 99.99 |
| 110 | 627 | 0.00 | 99.99 | 0.01 | 0.00 | 0.00 | 0.00 |
| 111 | 490 | 0.00 | 0.01 | 99.99 | 0.00 | 0.00 | 0.00 |
| 112 | 2388 | 88.45 | 0.14 | 0.01 | 0.00 | 9.83 | 0.31 |
| 113 | 287 | 3.46 | 0.09 | 0.00 | 0.00 | 2.90 | 93.16 |
| 114 | 500 | 42.78 | 0.59 | 0.01 | 0.00 | 46.92 | 3.70 |
| 115 | 1899 | 99.96 | 0.02 | 0.00 | 0.01 | 0.01 | 0.00 |
| 116 | 11 | 0.01 | 0.00 | 0.00 | 0.01 | 0.01 | 99.97 |

Heat exchanger (8) transfers 6,000 kW heat from the second bottoms stream (109) to the extract stream (104). The reboilers of the extractive distillation column (3), the solvent recovery distillation column (4), the isomer separation distillation column (5) and the light impurity distillation column (21) have heat demands of 3,114 kW, 2,729 kW, 705 kW and 802 kW respectively, leading to a total heat demand of 7.35 MW for the process of the invention with heat integration by heat exchanger (8), compared to a total heat demand of 13.35 MW for a process without such heat integration. Additional heat integration by heat transfer from the second bottoms stream to the column reboilers of the isomer separation distillation column and the light impurity distillation column can further reduce the total heat demand to 5.84 MW (5.23 kW/kg recovered methoxypropanols).

Example 2

The calculation of example 1 was repeated for an aqueous effluent stream comprising 95.73 wt.-% water, 2.06 wt.-% 1-methoxy-2-propanol (1MPOL), 1.51 wt.-% 2-methoxy-1-propanol (2MPOL), 0.01 wt.-% 1,2-propanediol (DIOL), 0.63 wt.-% methanol and 0.06 wt.-% other components, 1-nonanol (1NON) as extraction solvent, a weight ratio of extraction solvent stream to aqueous effluent stream of about 2.4 in the extraction and a weight ratio of extraction solvent to extract stream of about 0.25 in the extractive distillation. Table 2 shows the calculated flow rates and composition of streams in the process.

TABLE 2

| Stream No. | Total flow kg/h | $H_2O$ wt.-% | 1MPOL wt.-% | 2MPOL wt.-% | DIOL wt.-% | MeOH wt.-% | 1NON wt.-% |
|---|---|---|---|---|---|---|---|
| 101 | 29091 | 95.73 | 2.06 | 1.51 | 0.01 | 0.63 | 0.00 |
| 102 | 70000 | 0.01 | 0.00 | 0.02 | 0.00 | 0.00 | 99.79 |
| 103 | 24973 | 99.55 | 0.01 | 0.04 | 0.01 | 0.27 | 0.03 |

TABLE 2-continued

| Stream No. | Total flow kg/h | H$_2$O wt.-% | 1MPOL wt.-% | 2MPOL wt.-% | DIOL wt.-% | MeOH wt.-% | 1NON wt.-% |
|---|---|---|---|---|---|---|---|
| 104 | 74118 | 4.04 | 0.80 | 0.59 | 0.00 | 0.16 | 94.23 |
| 105 | 18173 | 0.01 | 0.00 | 0.02 | 0.00 | 0.00 | 99.79 |
| 106 | 3240 | 92.36 | 0.19 | 0.04 | 0.00 | 3.58 | 3.78 |
| 107 | 89052 | 0.00 | 0.66 | 0.50 | 0.00 | 0.00 | 98.66 |
| 108 | 1016 | 0.00 | 58.09 | 41.91 | 0.00 | 0.00 | 0.00 |
| 109 | 88036 | 0.00 | 0.00 | 0.02 | 0.00 | 0.00 | 99.80 |
| 110 | 590 | 0.00 | 99.99 | 0.01 | 0.00 | 0.00 | 0.00 |
| 111 | 426 | 0.00 | 0.01 | 99.99 | 0.00 | 0.00 | 0.00 |
| 112 | 3112 | 95.98 | 0.19 | 0.04 | 0.00 | 3.69 | 0.05 |
| 113 | 128 | 4.13 | 0.12 | 0.02 | 0.00 | 0.99 | 94.68 |
| 114 | 500 | 73.27 | 1.08 | 0.11 | 0.00 | 22.92 | 2.53 |
| 115 | 2623 | 99.90 | 0.02 | 0.03 | 0.00 | 0.01 | 0.00 |
| 116 | 11 | 0.01 | 0.00 | 0.02 | 0.00 | 0.00 | 99.79 |

Heat exchanger (8) transfers 6,000 kW heat from the second bottoms stream (109) to the extract stream (104). The reboilers of the extractive distillation column (3), the solvent recovery distillation column (4), the isomer separation distillation column (5) and the light impurity distillation column (21) have heat demands of 4,893 kW, 4,615 kW, 663 kW and 1003 kW respectively, leading to a total heat demand of 11.17 MW for the process of the invention with heat integration by heat exchanger (8), compared to a total heat demand of 17.17 MW for a process without such heat integration. Additional heat integration by heat transfer from the second bottoms stream to the column reboilers of the isomer separation distillation column and the light impurity distillation column can further reduce the total heat demand to 9.51 MW (9.36 kW/kg recovered methoxypropanols).

Example 3

The calculation of example 2 was repeated for 4-methylbenzylalcohol (4MBA) as extraction solvent and extraction at 65° C., a weight ratio of extraction solvent stream to aqueous effluent stream of about 2.75 in the extraction and a weight ratio of extraction solvent to extract stream of about 0.43 in the extractive distillation. Table 3 shows the calculated flow rates and composition of streams in the process.

Heat exchanger (8) transfers 5,500 kW heat from the second bottoms stream (109) to the extract stream (104). The reboilers of the extractive distillation column (3), the solvent recovery distillation column (4), the isomer separation distillation column (5) and the light impurity distillation column (21) have heat demands of 2,475 kW, 4,469 kW, 673 kW and 890 kW respectively, leading to a total heat demand of 8.51 MW for the process of the invention with heat integration by heat exchanger (8), compared to a total heat demand of 14.01 MW for a process without such heat integration. Additional heat integration by heat transfer from the second bottoms stream to the column reboilers of the isomer separation distillation column and the light impurity distillation column can further reduce the total heat demand to 6.94 MW (6.71 kW/kg recovered methoxypropanols).

Example 4

The calculation of example 2 was repeated for benzophenone (Ph2CO) as extraction solvent and extraction at 65° C., a weight ratio of extraction solvent stream to aqueous effluent stream of about 8.6 in the extraction, a weight ratio of extraction solvent to extract stream of about 0.14 in the extractive distillation and feed of purge stream 116 to the light impurity distillation column. Table 4 shows the calculated flow rates and composition of streams in the process.

TABLE 3

| Stream No. | Total flow kg/h | H$_2$O wt.-% | 1MPOL wt.-% | 2MPOL wt.-% | DIOL wt.-% | MeOH wt.-% | 4MBA wt.-% |
|---|---|---|---|---|---|---|---|
| 101 | 29091 | 95.73 | 2.06 | 1.51 | 0.01 | 0.63 | 0.00 |
| 102 | 80000 | 0.27 | 0.00 | 0.00 | 0.00 | 0.03 | 99.54 |
| 103 | 26222 | 99.55 | 0.00 | 0.01 | 0.01 | 0.08 | 0.28 |
| 104 | 82869 | 2.37 | 0.72 | 0.53 | 0.00 | 0.22 | 96.00 |
| 105 | 35536 | 0.27 | 0.00 | 0.00 | 0.00 | 0.03 | 99.54 |
| 106 | 2436 | 84.47 | 0.04 | 0.01 | 0.00 | 8.03 | 7.39 |
| 107 | 115969 | 0.00 | 0.51 | 0.38 | 0.00 | 0.00 | 98.95 |
| 108 | 1035 | 0.00 | 57.84 | 42.16 | 0.00 | 0.00 | 0.00 |
| 109 | 114934 | 0.00 | 0.00 | 0.00 | 0.00 | 0.00 | 99.84 |
| 110 | 599 | 0.00 | 99.99 | 0.01 | 0.00 | 0.00 | 0.00 |
| 111 | 436 | 0.00 | 0.01 | 99.99 | 0.00 | 0.00 | 0.00 |
| 112 | 2264 | 90.66 | 0.04 | 0.01 | 0.00 | 8.36 | 0.87 |
| 113 | 172 | 3.11 | 0.02 | 0.01 | 0.00 | 3.76 | 93.04 |
| 114 | 501 | 64.33 | 0.14 | 0.02 | 0.00 | 32.09 | 3.32 |
| 115 | 1423 | 99.94 | 0.00 | 0.01 | 0.00 | 0.00 | 0.00 |
| 116 | 1 | 0.27 | 0.00 | 0.00 | 0.00 | 0.03 | 99.54 |

TABLE 4

| Stream No. | Total flow kg/h | H₂O wt.-% | 1MPOL wt.-% | 2MPOL wt.-% | DIOL wt.-% | MeOH wt.-% | Ph2CO wt.-% |
|---|---|---|---|---|---|---|---|
| 101 | 29091 | 95.73 | 2.06 | 1.51 | 0.01 | 0.63 | 0.00 |
| 102 | 250000 | 0.10 | 0.00 | 0.00 | 0.00 | 0.02 | 99.80 |
| 103 | 27168 | 99.77 | 0.02 | 0.04 | 0.01 | 0.09 | 0.00 |
| 104 | 251923 | 0.39 | 0.24 | 0.17 | 0.00 | 0.08 | 99.04 |
| 105 | 35578 | 0.10 | 0.00 | 0.00 | 0.00 | 0.02 | 99.80 |
| 106 | 1244 | 82.01 | 0.04 | 0.01 | 0.00 | 17.54 | 0.31 |
| 107 | 286258 | 0.00 | 0.21 | 0.015 | 0.00 | 0.00 | 99.56 |
| 108 | 1023 | 0.00 | 58.17 | 41.83 | 0.00 | 0.00 | 0.00 |
| 109 | 285235 | 0.00 | 0.00 | 0.00 | 0.00 | 0.00 | 99.92 |
| 110 | 595 | 0.00 | 99.99 | 0.01 | 0.00 | 0.00 | 0.00 |
| 111 | 428 | 0.00 | 0.02 | 99.98 | 0.00 | 0.00 | 0.00 |
| 112 | 902 | 82.14 | 0.04 | 0.01 | 0.00 | 17.56 | 0.16 |
| 113 | 2 | 0.77 | 0.01 | 0.00 | 0.00 | 4.65 | 94.54 |
| 114 | 502 | 67.89 | 0.08 | 0.02 | 0.00 | 31.56 | 0.35 |
| 115 | 401 | 99.77 | 0.00 | 0.00 | 0.00 | 0.00 | 0.17 |
| 116 | 1 | 0.10 | 0.00 | 0.00 | 0.00 | 0.02 | 99.80 |

Heat exchanger (8) transfers 12,500 kW heat from the second bottoms stream (109) to the extract stream (104). The reboilers of the extractive distillation column (3), the solvent recovery distillation column (4), the isomer separation distillation column (5) and the light impurity distillation column (21) have heat demands of 11,115 kW, 19,362 kW, 667 kW and 855 kW respectively, leading to a total heat demand of 32.00 MW for the process of the invention with heat integration by heat exchanger (8), compared to a total heat demand of 44.50 MW for a process without such heat integration. Additional heat integration by heat transfer from the second bottoms stream to the column reboilers of the isomer separation distillation column and the light impurity distillation column can further reduce the total heat demand to 30.47 MW (29.8 kW/kg recovered methoxypropanols).

Heat exchanger (8) transfers 10,000 kW heat from the second bottoms stream (109) to the extract stream (104). The reboilers of the extractive distillation column (3), the solvent recovery distillation column (4), the isomer separation distillation column (5) and the light impurity distillation column (21) have heat demands of 19,034 kW, 26,760 kW, 657 kW and 829 kW respectively, leading to a total heat demand of 47.28 MW for the process of the invention with heat integration by heat exchanger (8), compared to a total heat demand of 57.28 MW for a process without such heat integration. Additional heat integration by heat transfer from the second bottoms stream to the column reboilers of the isomer separation distillation column and the light impurity distillation column can further reduce the total heat demand to 45.79 MW (45.6 kW/kg recovered methoxypropanols).

Example 5

The calculation of example 2 was repeated for methyl octadecanoate (C18FAME) as extraction solvent and extraction at 50° C., a weight ratio of extraction solvent stream to aqueous effluent stream of about 6.8 in the extraction and a weight ratio of extraction solvent to extract stream of about 0.10 in the extractive distillation. Table 5 shows the calculated flow rates and composition of streams in the process.

LIST OF REFERENCE SIGNS

| Device features: |
|---|
| 1 Countercurrent extraction column |
| 2 Feed inlet of the countercurrent extraction column |
| 3 Extractive distillation column |
| 4 Solvent recovery distillation column |
| 5 Isomer separation distillation column |
| 6 Overhead product outlet of the isomer separation distillation column |

TABLE 5

| Stream No. | Total flow kg/h | H₂O wt.-% | 1MPOL wt.-% | 2MPOL wt.-% | DIOL wt.-% | MeOH wt.-% | C18FAME wt.-% |
|---|---|---|---|---|---|---|---|
| 101 | 29091 | 95.73 | 2.06 | 1.51 | 0.01 | 0.63 | 0.00 |
| 102 | 199000 | 0.00 | 0.00 | 0.01 | 0.00 | 0.00 | 99.92 |
| 103 | 27058 | 99.80 | 0.02 | 0.06 | 0.01 | 0.01 | 0.02 |
| 104 | 201033 | 0.42 | 0.30 | 0.22 | 0.00 | 0.09 | 98.90 |
| 105 | 20171 | 0.00 | 0.00 | 0.01 | 0.00 | 0.00 | 99.92 |
| 106 | 1034 | 81.62 | 1.01 | 0.05 | 0.00 | 17.26 | 0.01 |
| 107 | 220169 | 0.00 | 0.27 | 0.20 | 0.00 | 0.00 | 99.46 |
| 108 | 1005 | 0.00 | 58.01 | 41.94 | 0.00 | 0.05 | 0.00 |
| 109 | 219164 | 0.00 | 0.00 | 0.01 | 0.00 | 0.00 | 99.92 |
| 110 | 583 | 0.00 | 99.91 | 0.00 | 0.00 | 0.08 | 0.00 |
| 111 | 422 | 0.00 | 0.12 | 99.88 | 0.00 | 0.00 | 0.00 |
| 112 | 1034 | 81.62 | 1.01 | 0.05 | 0.00 | 17.26 | 0.01 |
| 113 | 0 | | | | | | |
| 114 | 500 | 62.05 | 2.08 | 0.09 | 0.00 | 35.69 | 0.00 |
| 115 | 535 | 99.76 | 0.00 | 0.00 | 0.00 | 0.00 | 0.00 |
| 116 | 11 | 0.00 | 0.00 | 0.01 | 0.00 | 0.00 | 99.92 |

| | Device features: |
|---|---|
| 7 | Bottoms product outlet of the isomer separation distillation column |
| 8 | Heat exchanger |
| 9 | Conduit connecting the extract outlet of the countercurrent extraction column with the inlet of the heat uptake side of the heat exchanger |
| 10 | Conduit connecting the outlet of the heat uptake side of the heat exchanger with the feed inlet of the extractive distillation column |
| 11 | Conduit connecting the bottoms product outlet of the extractive distillation column with the feed inlet of the solvent recovery distillation column |
| 12 | Conduit connecting the overhead product outlet of the solvent recovery distillation column with the feed inlet of the of the isomer separation distillation column |
| 13 | Conduit connecting the bottoms product outlet of the solvent recovery distillation column with the inlet of the heat supply side of the heat exchanger |
| 14 | Conduit connecting the outlet of the heat supply side of the heat exchanger with the extraction solvent inlet of the countercurrent extraction column |
| 15 | Conduit connecting the outlet of the heat supply side of the heat exchanger with the extraction solvent inlet of the extractive distillation column |
| 16 | Overhead condenser |
| 17 | Phase separation vessel |
| 18 | Conduit connecting the overhead product outlet of the extractive distillation column with the inlet of the overhead condenser |
| 19 | Conduit connecting the outlet of the overhead condenser with the inlet of the phase separation vessel |
| 20 | Conduit connecting the outlet for organic phase of the phase separation vessel with conduit (13) or the conduit (15) |
| 21 | Light impurity distillation column |
| 22 | Overhead product outlet of the light impurity distillation column |
| 23 | Bottoms product outlet of the light impurity distillation column |
| 24 | Conduit connecting the outlet for aqueous phase of the phase separation vessel with the feed inlet of the light impurity distillation column |
| 25 | Coalescer |
| 26 | Phase separator |
| 27 | Outlet for aqueous phase of the phase separator |
| 28 | Conduit connecting the raffinate outlet of the countercurrent extraction column with the inlet of the coalesce |
| 29 | Conduit connecting the outlet of the coalescer with the inlet of the phase separator |
| 30 | Conduit connecting the outlet for organic phase of the phase separator with the extraction solvent inlet of the countercurrent extraction column |

| | Process features: |
|---|---|
| 101 | Aqueous effluent stream |
| 102 | Extraction solvent stream to countercurrent extraction column |
| 103 | Raffinate stream |
| 104 | Extract stream |
| 105 | Extraction solvent to extractive distillation column |
| 106 | First overhead stream |
| 107 | First bottoms stream |
| 108 | Second overhead stream |
| 109 | Second bottoms stream |
| 110 | Third overhead stream |
| 111 | Third bottoms stream |
| 112 | Aqueous phase stream |
| 113 | Organic phase stream |
| 114 | Fourth overhead stream |
| 115 | Fourth bottoms stream |
| 116 | Purge stream (not shown in the figure) |

The invention claimed is:

1. A process for recovering 1-methoxy-2-propanol and 2-methoxy-1-propanol from an aqueous effluent stream, the process comprising:
a) extracting said aqueous effluent stream with an extraction solvent stream in a countercurrent extraction column at a temperature of from 20 to 60° C., to provide a raffinate stream and an extract stream,
b) heating said extract stream by passing it through a heat exchanger on a heat uptake side of the heat exchanger, to provide a heated extract stream,
c) subjecting the heated extract stream to an extractive distillation in an extractive distillation column having an inlet for extraction solvent above an inlet for said heated extract stream, to provide a first overhead stream enriched in water and a first bottoms stream depleted in water relative to said heated extract stream,
d) distilling said first bottoms stream in a solvent recovery distillation column, to provide a second overhead stream comprising 1-methoxy-2-propanol and 2 methoxy-1-propanol and a second bottoms stream comprising recovered extraction solvent,
e) distilling said second overhead stream in an isomer separation distillation column, to provide a third overhead stream comprising 1-methoxy-2-propanol and a third bottoms stream comprising 2-methoxy-1-propanol,
f) cooling said second bottoms stream by passing it through said heat exchanger on a heat delivery side of the heat exchanger, to provide a recovered extraction solvent stream, and
g) passing a part of said recovered extraction solvent stream as the extraction solvent stream to a) and a part of said recovered extraction solvent stream as extraction solvent to the inlet for extraction solvent in c).

2. The process of claim 1, wherein said extraction solvent comprises at least one hydrogen acceptor functional group and has a solubility in water at 20° C. of less than 1 g/kg and a boiling point at 1 bar of at least 160° C.

3. The process of claim 2, wherein the hydrogen acceptor functional group is selected from the group consisting of an aliphatic hydroxyl group, a ketone carbonyl group, a sulfoxide group, a sulfone group, a carboxamide group, a phosphine oxide group, a phosphoric ester group, and a combination thereof.

4. The process of claim 3, wherein the extraction solvent is an aliphatic alcohol having from 7 to 14 carbon atoms.

5. The process of claim 4, wherein the extraction solvent is 2-ethylhexanol.

6. The process of claim 1, wherein said aqueous effluent stream comprises 1-methoxy-2 propanol and 2-methoxy-1-propanol in a combined amount of from 1 to 10% by weight.

7. The process of claim 1, wherein said aqueous effluent stream comprises from 0.1 to 5% by weight of methanol.

8. The process of claim 1, wherein
the extraction solvent forms a heteroazeotrope with water,
the first overhead stream is condensed and separated into an aqueous phase stream and an organic phase stream, and
the organic phase stream is either combined with the second bottoms stream or passed to c) for supplying extraction solvent.

9. The process of claim 8, wherein the aqueous phase stream is distilled in a light impurity distillation column to provide a fourth overhead stream enriched in compounds which are more volatile than water, compared to said aqueous phase stream.

10. The process of claim 1, wherein the raffinate stream is passed through a coalescer containing nets, meshes, or packings of hydrophobic fibers or a packing with a hydrophobic surface, and an organic phase separated from said raffinate stream is recycled to a) for supplying extraction solvent.

11. A facility for recovering 1-methoxy-2-propanol and 2-methoxy-1-propanol from an aqueous effluent stream, comprising:
- a countercurrent extraction column having a feed inlet, an extraction solvent inlet, a raffinate outlet, and an extract outlet;
- an extractive distillation column having a feed inlet, an extraction solvent inlet above the feed inlet, an overhead product outlet, and a bottoms product outlet;
- a solvent recovery distillation column having a feed inlet, an overhead product outlet, and a bottoms product outlet;
- an isomer separation distillation column having a feed inlet, an overhead product outlet, and a bottoms product outlet;
- a heat exchanger having a heat supply side and a heat uptake side, each having an inlet and an outlet;
- a conduit connecting the extract outlet of the countercurrent extraction column with the inlet of the heat uptake side of the heat exchanger;
- a conduit connecting the outlet of the heat uptake side of the heat exchanger with the feed inlet of the extractive distillation column;
- a conduit connecting the bottoms product outlet of the extractive distillation column with the feed inlet of the solvent recovery distillation column;
- a conduit connecting the overhead product outlet of the solvent recovery distillation column with the feed inlet of the isomer separation distillation column;
- a conduit connecting the bottoms product outlet of the solvent recovery distillation column with the inlet of the heat supply side of the heat exchanger; and
- a conduit connecting the outlet of the heat supply side of the heat exchanger with each of the extraction solvent inlet of the countercurrent extraction column and the extraction solvent inlet of the extractive distillation column.

12. The facility of claim 11, additionally comprising:
an overhead condenser having an inlet and an outlet;
- a phase separation vessel having an inlet, an outlet for organic phase, and an outlet for aqueous phase;
- a conduit connecting the overhead product outlet of the extractive distillation column with the inlet of the overhead condenser;
- a conduit connecting the outlet of the overhead condenser with the inlet of the phase separation vessel; and
- a conduit connecting the outlet for organic phase of the phase separation vessel with
  - the conduit connecting the bottoms product outlet of the solvent recovery distillation column with the inlet of the heat supply side of the heat exchanger, or
  - the conduit connecting the outlet of the heat supply side of the heat exchanger with the extraction solvent inlet of the extractive distillation column.

13. The facility of claim 12, additionally comprising:
- a light impurity distillation column having a feed inlet, an overhead product outlet, and a bottoms product outlet; and
- a conduit connecting the outlet for aqueous phase of the phase separation vessel with the feed inlet of the light impurity distillation column.

14. The facility of claim 11, additionally comprising:
- a coalescer having an inlet and an outlet;
- a phase separator having an inlet, an outlet for organic phase, and an outlet for aqueous phase;
- a conduit connecting the raffinate outlet of the countercurrent extraction column with the inlet of the coalescer;
- a conduit connecting the outlet of the coalescer with the inlet of the phase separator; and
- a conduit connecting the outlet for organic phase of the phase separator with the extraction solvent inlet of the countercurrent extraction column.

* * * * *